(12) United States Patent
Herron et al.

(10) Patent No.: US 6,806,390 B1
(45) Date of Patent: Oct. 19, 2004

(54) HYDROPEROXIDE DECOMPOSITION CATALYST

(75) Inventors: Norman Herron, Newark, DE (US); Stephan Schwarz, Wilmington, DE (US); Joe Douglas Druliner, Newark, DE (US)

(73) Assignee: Inuista North America S.àr.l.

( * ) Notice: Subject to any disclaimer, the term of this patent is extended or adjusted under 35 U.S.C. 154(b) by 0 days.

(21) Appl. No.: 10/344,443

(22) PCT Filed: Aug. 18, 2000

(86) PCT No.: PCT/US00/22867

§ 371 (c)(1),
(2), (4) Date: Feb. 11, 2003

(87) PCT Pub. No.: WO02/16296

PCT Pub. Date: Feb. 28, 2002

(51) Int. Cl.[7] .......................... C07C 45/41; C07C 29/20
(52) U.S. Cl. ................. 568/342; 568/344; 568/346; 568/835; 568/836
(58) Field of Search ................................ 568/342, 344, 568/346, 835, 836

(56) References Cited

U.S. PATENT DOCUMENTS

| | | |
|---|---|---|
| 2,722,504 A | 11/1955 | Fleck et al. |
| 3,927,108 A | 12/1975 | Van De Moesdijk et al. |
| 4,238,415 A | 12/1980 | Bryan |
| 4,451,572 A | 5/1984 | Cody |
| 5,028,575 A | 7/1991 | Yates, Jr. et al. |
| 5,550,301 A | 8/1996 | Bhinde et al. |
| 6,284,927 B1 * | 9/2001 | Druliner et al. ............ 568/342 |

FOREIGN PATENT DOCUMENTS

| | | |
|---|---|---|
| WO | WO 98/34894 | 8/1998 |
| WO | WO 99/02264 | 1/1999 |

* cited by examiner

*Primary Examiner*—Johann Richter
*Assistant Examiner*—Sikarl A. Witherspoon

(57) ABSTRACT

An improved catalytic process for decomposing alkyl or aromatic hydroperoxides is disclosed which utilizes a caalytic amount of a heterogeneous Au catalyst that has been treated with an organosilicon reagent.

17 Claims, No Drawings

HYDROPEROXIDE DECOMPOSITION CATALYST

FIELD OF INVENTION

The invention generally relates to an improved catalytic process for decomposing alkyl or aromatic hydroperoxides to form a mixture containing the corresponding alcohol and ketone. In particular, the invention relates to decomposing a hydroperoxide by contacting it with a catalytic amount of a heterogeneous Au catalyst that has been treated with an organosilicon reagent.

BACKGROUND

Industrial processes for the production of mixtures of cyclohexanol and cyclohexanone from cyclohexane are currently of considerable commercial significance and are well described in the patent literature. In accordance with typical industrial practice, cyclohexane is oxidized to form a reaction mixture containing cyclohexyl hydroperoxide (CHHP). The resulting CHHP is either decomposed or hydrogenated, optionally in the presence of a catalyst, to form a reaction mixture containing cyclohexanol and cyclohexanone. In the industry, such a mixture is known as a K/A (ketone/alcohol) mixture, and can be readily oxidized to produce adipic acid or caprolactam, which are important reactants in processes for preparing certain condensation polymers, notably polyamides. A high K/A ratio in the reaction mixture is generally preferred. Due to the large volumes of adipic acid consumed in these and other processes, improvements in processes for producing adipic acid and its precursors can be used to provide beneficial cost advantages.

Druliner et al., (WO 98/34894) used a heterogeneous gold catalyst in an improved catalytic process for decomposing alkyl or aromatic hydroperoxides to form a mixture containing the corresponding alcohol and ketone.

Two common problems in CHHP processes, especially in heterogeneous catalytic processes, are the presence of water and acidic byproducts in the CHHP containing reaction mixture. Both of these can deactivate the catalysts, resulting in lower conversion rates and/or lower K/A ratios. One method to eliminate the acidic byproducts is by the addition of a neutralization agent, such as that described in U.S. Pat. No. 4,238,415. This, however, results in undesirable salts, which need to be removed from the final product. In situ drying of the reaction mixture to remove water has been used in both hydrogenation and decomposition processes (U.S. Pat. Nos. 5,550,301 and 3,927,108), but these methods do not remove the acidic by-products along with the water.

Organosilicon compounds have for some time been employed in the treatment of inorganic oxide surfaces such as inorganic oxide films, particulates and pigments, and fibers (such as glass fibers, aluminum fibers and steel fibers). The typical organosilicon treatment involves coating such surfaces with a hydrolyzate (and/or condensate of the hydrolyzate) of an organofunctional hydrolyzable silane. The treatment is typically supplied to the surface of the inorganic oxide whereby through the hydrolyzable groups or silanol groups (≡Si—OH), bonding through siloxy moieties (≡Si—O—) is effected.

U.S. Pat. No. 2,722,504 modified the contact efficiency of catalysts and other materials by the incorporation of alkyl silanes onto the surface.

U.S. Pat. No. 4,451,572 describes a surface modified zeolite produced by reacting the zeolite with an organosilane.

WO 99/02264 describes but does not exemplify a supported ultrafine gold particle catalyst that has been rendered hydrophobic for the synthesis of hydrogen peroxide, one method of which is by treatment with silane.

U.S. Pat. No. 5,029,575 describes a method of removing the surface hydroxyl groups from a $Rh/Al_2O_3$ catalyst by silation.

SUMMARY OF THE INVENTION

Disclosed herein is an improved process for decomposing a hydroperoxide to form a decomposition reaction mixture containing a corresponding alcohol and ketone, the improvement comprising decomposing the hydroperoxide by contacting the hydroperoxide with a catalytic amount of a heterogeneous gold catalyst wherein the gold catalyst has been silanized with an organosilicon reagent. Further disclosed is the process wherein the heterogenous catalyst is supported on a catalyst support member.

DETAILED DESCRIPTION OF THE INVENTION

The present invention provides an improved process for conducting a hydroperoxide decomposition step in an industrial process in which an alkyl or aromatic compound is oxidized to form a mixture of the corresponding alcohol and ketone. In particular, cyclohexane can be oxidized to form a mixture containing cyclohexanol (A) and cyclohexanone (K). The industrial process involves two steps: first, cyclohexane is oxidized, forming a reaction mixture containing CHHP; second, CHHP is decomposed, forming a mixture containing K and A. As previously mentioned, processes for the oxidation of cyclohexane are well known in the literature and available to those skilled in the art.

The improved process can also be used for the decomposition of other alkane or aromatic hydroperoxides, for example, t-butyl hydroperoxide, cyclododecylhydroperoxide and cumene hydroperoxide.

Advantages of the present heterogeneous catalytic process, relative to processes employing homogenous metal catalysts, such as metal salts or metal/ligand mixtures, include longer catalyst life, improved yields of useful products, and the absence of soluble metal compounds. However, the use of heterogeneous catalysts subject the process to fouling by water and organic impurities from the oxidation reaction, especially acidic impurities. Removal of these impurities prevents fouling of the catalyst, which thereby extends the catalyst lifetime.

The heterogeneous catalysts of the invention comprise Au and Au compounds, preferably applied to suitable solid supports, that have been silanized by an organosilicon reagent. The catalysts after treatment are extremely hydrophobic while showing no decrease in activity as compared to the untreated catalyst.

The inventive process may also be performed using Au in the presence of other metals, preferably metals of Periodic Group VIII, more preferably Pd. The metal to support percentage can vary from about 0.01 to about 50 percent by weight, and is preferably about 0.1 to about 10 wt. percent. Suitable and presently preferred supports include $SiO_2$ (silica), $Al_2O_3$ (alumina), C (carbon), $TiO_2$ (titania), MgO (magnesia) or $ZrO_2$ (zirconia). Alumina is a particularly preferred support, and Au supported on alumina is a particularly preferred catalyst of the invention. A preferred catalyst is 0.1–10% Au/0.05–2% Pd on α-alumina, more preferably 1% Au/0.1% Pd on α-alumina.

Some of the heterogeneous catalysts of the invention can be obtained already prepared from manufacturers, or they can be prepared from suitable starting materials using methods known in the art. Supported gold catalysts can be prepared by any standard procedure known to give well-dispersed gold, such as sol-gel techniques, evaporative techniques or coatings from colloidal dispersions.

In particular, ultra-fine particle sized gold is preferred. Such small particulate gold (often smaller than 10 nm) can be prepared according to Haruta, M., "Size-and Support-Dependency in the Catalysis of Gold", Catalysis Today 36 (1997) 153–166 and Tsubota et al., Preparation of Catalysts V, pp. 695–704 (1991). Such gold preparations produce samples that are purple-pink in color instead of the typical bronze color associated with gold and result in highly dispersed gold catalysts when placed on a suitable support member. These highly dispersed gold particles typically are from about 3 nm to about 25 nm in diameter.

The catalyst solid support, including $SiO_2$, $Al_2O_3$, carbon, MgO, zirconia, or $TiO_2$, can be amorphous or crystalline, or a mixture of amorphous and crystalline forms. Selection of an optimal average particle size for the catalyst supports will depend upon such process parameters as reactor residence time and desired reactor flow rates. Generally, the average particle size selected will vary from about 0.005 mm to about 5 mm. Catalysts having a surface area larger than 10 $m^2/g$ are preferred since increased surface area of the catalyst has a direct correlation with increased decomposition rates in batch experiments. Supports having much larger surface areas can also be employed, but inherent brittleness of high-surface area catalysts, and attendant problems in maintaining an acceptable particle size distribution, will establish a practical upper limit upon catalyst support surface area. A preferred support is alumina; more preferred is α-alumina and γ-alumina.

Adding air or a mixture of air and inert gases to CHHP decomposition mixtures provides higher conversions of process reactants to K and A, since some cyclohexane is oxidized directly to K and A, in addition to K and A being formed by CHHP decomposition. This ancillary process is known as "cyclohexane participation", and is described in detail in Druliner et al., U.S. Pat. No. 4,326,084, the entire contents of which are incorporated by reference herein. Other gases may also be added or co-fed to the reaction mixture as needed. Inert gases such as nitrogen may also be added to the reaction alone or in combination with other gases.

The results of the CHHP decomposition reaction, such as the K/A ratio or conversion rate, can be adjusted by choice of catalyst support, gases added to the reaction mixture, or metals added to the the heterogenous catalysts of the invention.

Preferably, metals added to the heterogenous catalysts of the invention are for use as promoters, synergist additives, or co-catalysts are selected from Periodic Group VIII, hereby defined as Fe, Co, Ni, Ru, Rh, Pd, Os, Ir, and Pt. Most preferred is Pd and Pt.

One preferred gas that can be added to the reaction mixture is hydrogen. An advantage of the addition of hydrogen is that the K/A ratio can be varied according to need. The addition of hydrogen can also convert impurities or by-products of the reactions, such as benzene, to more desirable products.

In practice of the invention, the catalysts can be contacted with CHHP by formulation into a catalyst bed, which is arranged to provide intimate contact between catalysts and reactants. Alternatively, catalysts can be slurried with reaction mixtures using techniques known in the art. The process of the invention is suitable for batch or for continuous CHHP decomposition processes. These processes can be performed under a wide variety of conditions.

'Silanized' is defined herein to refer to treatment of the catalyst with either at least one silane, or a mixture of at least one silane and at least one polysiloxane (collectively referred to herein as organosilicon compounds).

Suitable silanes have the formula $R_xSi(R')_{4-x}$ wherein R is a nonhydrolyzable aliphatic, cycloaliphatic or aromatic group having at least 8 to about 20 carbon atoms; R' is a hydrolyzable group such as but not limited to alkoxy, halogen, acyloxy, acetoxy, hydroxy or mixtures thereof; and x=1 to 3.

For example, silanes useful in carrying out the invention include octyltriethoxysilane, nonyltriethoxysilane, decyltriethoxysilane, dodecyltriethoxysilane, tridecyltriethoxysilane, tetradecyltriethoxysilane, pentadercyltriethoxysilane, hexadecyltriethoxysilane, heptadecyltriethoxysilane and octadecyltriethoxysilane. Preferred examples of silanes include R=8–10 carbon atoms; R'=chloro, ethoxy, methoxy, hydroxy or mixtures thereof; and x=1 to 3. Most preferred silanes are R=8 carbon atoms; R'=ethoxy; and x=3. Mixtures of silanes are contemplated equivalents. Weight content of the silane, based on total silanized catalyst is typically about 0.05 to about 3 weight %, preferably about 0.1 to about 2 weight %.

In an alternative embodiment, a mixture of at least one silane with at least one polysiloxane is useful in carrying out the invention. Suitable polysiloxanes have the formula:

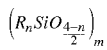

wherein R is organic or inorganic groups; n=0–3; and m≦2.

For example, polydimethylsiloxane (PDMS), vinyl phenylmethyl terminated dimethyl siloxanes, divinylmethyl terminated polydimethyl siloxane and the like are suitable polysiloxanes. PDMS is a preferred polysiloxane. The silane useful in the mixture may be the silane described above with R=8–20 carbon atoms, R'=alkoxy and x=1 preferred. Weight content of the silane and polysiloxane, is about 0.1 to about 5.0 weight %, preferably from about 0.2 to 3 weight %. The ratio of silane to polysiloxane can be 1 silane:2 polysiloxane up to 2 silane:1 polysiloxane.

The silanes and polysiloxanes are commercially available or can be prepared by processes known in the art such as those described in "Organosilicon Compounds", S. Pawlenko, et al., New York (1980). The method of addition is not especially critical and the catalyst may be treated with the silane in a number of ways. For example, the silane addition can be made neat or prehydrolyzed to a dry base, from a slurry, a filtration step, during drying or at a size operation such as a fluid energy mill, e.g., micronizer, or media mill as described in greater detail in Niedenzu, et al, U.S. Pat. No. 5,501,732, or post blending after micronizing. The polysiloxane addition can be made in conjunction with the silane or post addition to the silanized support.

An alternate embodiment that is contemplated is the use of other members of Periodic Groups IV and V in place of Si, such as Ge, P, and As. The catalysts of the invention would thereby be treated with compounds that are the equivalent of the silanes of the instant invention, such as $R_xGe(R')_{4-x}$, $R_xP(R')_{3-x}^-$, etc.

The following definitions are used herein and should be referred to for claim interpretation.

A Cyclohexanol
CB Chlorobenzene
CHHP Cyclohexylhydroperoxide
K Cyclohexanone
OTES Octyltriethoxysilane $(SiC_8H_{17}(CH_3CH_2O)_3)$ The following non-limiting Examples are meant to illustrate the invention but are not intended to limit it in any way.

EXAMPLES

All catalysts were prepared by Engelhard Corp., 1729 East Avenue, Erie, Pa. 19503 for E. I. du Pont de Nemours and Company, using a proprietary procedure based on the general procedure shown below.

10 g–60 mesh α-alumina was slurried into a solution of 0.2 g gold chloride and 0.02 g palladium tetraamine chloride in 50 mL water and one drop of conc. HCl. The slurry was stirred gently as the pH was adjusted to 9.6 with 0.1 M sodium carbonate solution. The slurry was again stirred gently while 0.69 g sodium citrate solid was slowly added and then stirred for 2 further hours. After filtering and washing well with distilled water, the solid was calcined in flowing air for 5 hours at 250° C.

In Examples 1–7 (Table I) vials were analyzed directly for the amount of CHHP remaining, using a 15 m DB-17 capillary column with a 0.32 mm internal diameter. The liquid phase of the column was comprised of (50 wt % phenyl) methyl polysiloxane. The column was obtained from J. and W. Scientific, Folsum, Va.

GC analyses for the amounts of CHHP in each solution were calculated using the equation:

wt. % CHHP=(area % CHHP/area % CB)×wt. % CB×R.F.$_{CHHP}$

R.F.$_{CHHP}$ (GC response factor for CHHP) and % CHHP decomposition were determined from calibration solutions containing known amounts of CHHP and CB, and was calculated from the equations:

$$R.F._{CHHP} = \frac{wt~\%~CHHP/\text{area}~\%~CHHP}{wt~\%~CB/\text{area}~\%~CB}$$

$$\%CHHP~\text{decomposition} = 100 \times \left[1 - \frac{(\text{area}~\%~CHHP/\text{area}~\%~CB)_{final}}{(\text{area}~\%~CHHP/\text{area}~\%~CB)_{initial}}\right]$$

In Examples 1–7 (Table I) the initial concentrations of CHHP in each vial were approximately 2 wt %. The GC wt % CHHP$_{initial}$ and CHHP$_{final}$ numbers are only approximate because the amount of CB per g solution ratios used in GC calculations were arbitrarily all made equal to 0.25 mg CB/g solution. Since an unheated sample of 1.5 mL n-tetradecane and 30 μL CHHP/CB solution was analyzed with each set of CHHP decomposition product vials made from the same CHHP/CB solution, accurate changes in CHHP/CB ratios could be calculated.

Experiment 1

Preparation of ~2 wt % Octyl Derivatized Catalyst 10 g of catalyst (1% Au;0.1% Pd on 2 mm α-alumina spheres) was slurried into 25 mL dry toluene in a nitrogen filled glove box. 0.1 mL water was added and the slurry stirred for 30 mins. 0.33 g of silanizing reagent octyltriethoxysilane (OTES) was added to the solution which was then capped and tumbled slowly in a 70° C. water bath for 4 hrs under house vacuum. The slurry was then filtered and the spheres collected, washed with 100 mL ethanol and then 50 mL acetone and suction dried. They were then dried at 110° C. in flowing air for 1 hour before collecting and testing in CHHP decomposition. The recovered catalyst is extremely hydrophobic and did not wet when immersed in water.

Experiment 2

Preparation of ~0.6 wt % octyl derivatized Catalyst 10 g of catalyst (1% Au;0.1% Pd on 2 mm α-alumina spheres) was slurried into 25 mL dry toluene in a nitrogen filled glove box. 0.1 mL water was added and the slurry stirred for 30 mins. 0.1 g (OTES) was added to the solution which was then capped and tumbled slowly in a 70° C. water bath for 4 hrs under house vacuum. The slurry was then filtered and the spheres collected, washed with 100 mL ethanol and then 50 mL acetone and suction dried. They were then dried at 110° C. in flowing air for 1 hour before collecting and testing in CHHP decomposition. The recovered catalyst is extremely hydrophobic and did not wet when immersed in water.

Experiment 3

Preparation of ~15 wt % Octyl Derivatized Catalyst 10 g of catalyst (1% Au;0.1% Pd on 2 mm α-alumina spheres) was slurried into 25 mL dry toluene in a nitrogen filled glove box. 0.1 mL water was added and the slurry stirred for 30 mins. 0.025 g (OTES) was added to the solution which was then capped and tumbled slowly in a 70° C. water bath for 4 hrs under house vacuum. The slurry was then filtered and the spheres collected, washed with 100 mL ethanol and then 50 mL acetone and suction dried. They were then dried at 110° C. in flowing air for 1 hour before collecting and testing in CHHP decomposition. The recovered catalyst is extremely hydrophobic and did not wet when immersed in water.

Examples 1–7

Batch Decomposition of CHHP Using Hydrophobically Modified Catalysts

All reactions were run in batch reactor mode, in stirred 3.5 mL glass vials, sealed with septa and plastic caps. Vials were inserted into a block aluminum heater/stirrer apparatus that holds up to 8 vials. Stirring was done using Teflon®-coated stir bars. Each vial was first charged with 1.5 mL of n-tetradecane solvent, approximately 0.01 g of a given catalyst, a stir bar and the vial was sealed. Vials were stirred and heated approximately 10 minutes to assure that the desired reaction temperature of 150° C. had been attained. Next, at the start of each example, 30 μL of a stock solution of CHHP and CB (chlorobenzene), GC (gas chromatograph) internal standard, were injected. Stock solutions consisted of mixtures of about 20 wt % CB in CHHP. The CHHP source contained up to 2.0 wt % of combined cyclohexanol and cyclohexanone. Vials were removed from the aluminum heater/stirrer after a 4 or 8 minute period and were allowed to cool to ambient temperature. Results indicate that the silane reagent does not significantly reduce the catalytic activity of the gold catalysts.

TABLE I

| Ex. | Catalyst, g | Method of Prep | Approx Wt % CHHP | Reaction Temp., ° C. | Time, min. | Wt % CHHP initial | Wt % CHHP final | % CHHP Decomp. |
|---|---|---|---|---|---|---|---|---|
| 1 | (1% Au + 0.1% Pd)/α-Al$_2$O$_3$, 0.0141 | — | 2 | 150 | 4 | 4.69 | 3.57 | 24.0 |

TABLE I-continued

| Ex. | Catalyst, g | Method of Prep | Approx Wt % CHHP | Reaction Temp., °C. | Time, min. | Wt % CHHP initial | Wt % CHHP final | % CHHP Decomp. |
|---|---|---|---|---|---|---|---|---|
| 2 | (1% Au + 0.1% Pd)/α-Al$_2$O$_3$, 0.0126 | — | 2 | 150 | 4 | 4.69 | 2.93 | 37.4 |
| 3 | Derivatized(1% Au + 0.1% Pd)/α-Al$_2$O$_3$, 0.0133 | Exp. 1 | 2 | 150 | 4 | 4.69 | 3.06 | 34.8 |
| 4 | Derivatized(1% Au + 0.1% Pd)/α-Al$_2$O$_3$, 0.0132 | Exp. 1 | 2 | 150 | 4 | 4.69 | 3.89 | 17.0 |
| 5 | (1% Au + 0.1% Pd)/α-Al$_2$O$_3$, 0.0122 | — | 2 | 150 | 8 | 4.85 | 2.87 | 40.7 |
| 6 | Derivatized(1% Au + 0.1% Pd)/α-Al$_2$O$_3$, 0.0129 | Exp. 2 | 2 | 150 | 8 | 4.85 | 3.41 | 29.7 |
| 7 | Treated(1% Au + 0.1% Pd)/α-Al$_2$O$_3$, 0.0126 | Exp. 3 | 2 | 150 | 8 | 4.85 | 3.04 | 37.3 |

Examples 8–11

Continuous Reactor CHHP Decomposition in Presence of Water 2 g of catalyst from Experiment 1 above was loaded into a tubular reactor and packed between inert 'filler' particles. A flow of 6.5 to 6.9 mL/min of liquid cyclohexane oxidate was fed through the reactor at 150 to 175° C. and various amounts of water were added. Results in Table II indicate that the hydrophobic catalyst maintains its activity in the presence of up to 0.9% water in the feed although the ratio of ketone to alcohol produced falls as water is introduced.

TABLE II

| Ex. | Catalyst and feed | Method of Prep | Flow | Feed Temp., °C. | % CHHP Decomp. | Rate constant (g. feed/g. cat/hr) | dK/dA ratio |
|---|---|---|---|---|---|---|---|
| 8 | Catalyst alone | — | 6.5 | 175 | 97.9 | 603.6 | 1.66 |
| 9 | Catalyst alone | — | 6.5 | 150 | 70.8 | 190.9 | 1.20 |
| 10 | Catalyst + 0.5% Water | Exp. 1 | 6.5 | 150 | 76.4 | 223.7 | 0.71 |
| 11 | Catalyst + 0.9% Water | Exp. 1 | 6.9 | 150 | 60.9 | 154.5 | 0.59 |

We claim:

1. An improved process for decomposing a hydroperoxide to form a decomposition reaction mixture containing a corresponding alcohol and ketone, the improvement comprising decomposing the hydroperoxide by contacting the hydroperoxide with a catalytic amount of a heterogeneous gold catalyst wherein the gold catalyst has been silanized with an organosilicon reagent.

2. The process according to claim 1 wherein the heterogenous catalyst is supported on a catalyst support member.

3. The process according to claim 2 wherein the catalyst support member is selected from the group consisting of SiO$_2$, Al$_2$O$_3$, carbon, TiO$_2$, MgO, and zirconia.

4. The process according to claim 1 wherein the hydroperoxide is cyclohexylhydroperoxide.

5. The process according to claim 1 wherein the organosilicon reagent has the formula Rhd xSi(R')$_{4-x}$ wherein:

R is a nonhydrolyzable aliphatic, cycloaliphatic or aromatic group having at least 8 to about 20 carbon atoms;

R' is a hydrolyzable group selected from the group consisting of alkoxy, halogen, acyloxy, acetoxy, hydroxy and mixtures thereof; and x=1 to 3.

6. The process according to claim 5 wherein the organosilicon reagent further comprises a polysiloxane having the formula $$\left(R_n SiO_{\frac{4-n}{2}}\right)_m$$

wherein R is organic or inorganic groups; n=0–3; and m≦2.

7. The process according to claim 5 wherein the organosilicon reagent is present in the amount of about 0.05 to about 3 weight %.

8. The process according to claim 7 wherein the organosilicon reagent is present in the amount of about 0.1 to about 2 weight %.

9. The process according to claim 5 wherein:

R is octyl;

R$^3$ is ethoxy; and x=3.

10. The process according to claim 4 wherein the process is run in the presence of cyclohexane.

11. The process according to claim 4 wherein the process is run in the presence of added oxygen.

12. The process according to claim 3 wherein the gold is supported on alumina.

13. The process according to claim 12 wherein the gold is from about 0.1 to about 10 wt. percent of the catalyst and support member.

14. The process according to claim 13 wherein the gold is present on the support member as well-dispersed particles having a diameter from about 3 nm to about 25 nm.

15. The process according to claim 1 wherein a metal selected from Periodic Group VIII is also present with gold.

16. The process according to claim 15 wherein the metal is Pd or Pt.

17. The process according to claim 1 wherein the process is run in the presence of nitrogen or hydrogen.

* * * * *